United States Patent
Cho et al.

(10) Patent No.: US 7,744,919 B2
(45) Date of Patent: Jun. 29, 2010

(54) BLOCK COPOLYMER MICELLE COMPOSITION HAVING AN ENHANCED DRUG-LOADING CAPACITY AND SUSTAINED RELEASE

(75) Inventors: Kilwon Cho, Pohang-si (KR); Jae Young Lee, Pohang-si (KR)

(73) Assignee: Postech Foundation (KR)

( * ) Notice: Subject to any disclaimer, the term of this patent is extended or adjusted under 35 U.S.C. 154(b) by 101 days.

(21) Appl. No.: 10/526,836

(22) PCT Filed: May 30, 2003

(86) PCT No.: PCT/KR03/01065

§ 371 (c)(1), (2), (4) Date: Mar. 4, 2005

(87) PCT Pub. No.: WO2004/022036

PCT Pub. Date: Mar. 18, 2004

(65) Prior Publication Data

US 2005/0287196 A1    Dec. 29, 2005

(30) Foreign Application Priority Data

Sep. 4, 2002    (KR) .................... 10-2002-0053090

(51) Int. Cl.
*A61K 9/127*    (2006.01)

(52) U.S. Cl. .......................................... 424/450; 516/9
(58) Field of Classification Search ................. 424/450, 424/426, 424, 486, 501, 70.11
See application file for complete search history.

(56) References Cited

U.S. PATENT DOCUMENTS 5,702,717 A * 12/1997 Cha et al. .................. 424/425

OTHER PUBLICATIONS

Cammas et al., 1993, Macromolecules, 26, pp. 4681-4684.*
Jaeyoung Lee, et al., Incorporation and release behavior of hydrophobic drug . . . ; Journal of Controlled Release 94 (2004) 323-335.

* cited by examiner

*Primary Examiner*—Michael G Hartley
*Assistant Examiner*—James W Rogers
(74) *Attorney, Agent, or Firm*—Baker & Hostetler, LLP

(57) ABSTRACT

A micelle drug composition having an enhanced drug-loading capacity and improved sustained-release characteristics comprising an amphiphilic block copolymer including at least one hydrophilic blocks and at least one hydrophobic blocks. The block copolymer comprises functional groups selected from the group consisting of carboxyl, amine, hydroxyl, amide, thiol and sulfonic acid groups, in the hydrophobic block chain of the copolymer, and the average number of the functional groups range from 1.1 to 30.

6 Claims, No Drawings

BLOCK COPOLYMER MICELLE COMPOSITION HAVING AN ENHANCED DRUG-LOADING CAPACITY AND SUSTAINED RELEASE

FIELD OF THE INVENTION

The present invention relates to a micelle drug composition having an enhanced drug-loading capacity and improved sustained drug-release characteristics.

BACKGROUND OF THE INVENTION

Amphiphilic block copolymers that can form a core-shell type micelle in an aqueous medium have been used for delivering hydrophobic drugs such as anti-cancer drugs, adriamycin and paclitaxel, the drug being loaded in the hydrophobic core and the hydrophilic shell enhancing the solubilization of the micelle.

Such a micelle having a size of not more than 200 nm and a polyethyleneoxide hydrophilic shell is neither easily destroyed by the reticuloenthelial or mononuclear phagocyte system nor excreted through kidney, and therefore, circulates in a living body for a long period of time, accumulating at the blood vessel around tumors where the transfer of materials is much enhanced and more selective than that around normal cells.

The hydrophobic block of such amphiphilic block copolymers may be divided into two groups, i.e., (i) a hydrophobic block having no functional group, e.g. polylactide, polycarprolactone, poly(lactide-glycolide), poly(β-benzyl L-aspartate), as way disclosed in Korean Patent Publication Nos. 1999-69033 and 2001-105439, European Patent Publication No. 583055, U.S. Pat. No. 6,322,805 and Japanese Patent Publication No. 1994-206815, and (ii) a hydrophobic block having a plurality of functional groups, e.g., poly(β-substituted aspartate), poly(γ-substituted glutamate), poly(L-leucine), described in European Patent Publication No. 583955. In case the hydrophobic block has no functional group, the drug loading capacity of the hydrophobic core is limited, whereas when contains too much functional groups, for example, 300 or more per hydrophobic block, the amphiphilic nature of the copolymer is lost and dissolves in an aqueous medium and cannot form a micelle. Therefore, the step of chemically bonding a hydrophobic drug to such copolymer has been performed to prepare a delivery composition.

Accordingly, in order to solve this problem and increase the drug loading capacity and sustained-release characteristics of micelle drug composition, there has been a need to develop amphiphilic block copolymeric micelles containing a small quantity of functional groups in a hydrophobic block.

SUMMARY OF THE INVENTION

Accordingly, it is a primary object of the present invention to provide a micelle composition for drug delivery having an enhanced drug-loading capacity and sustained-release characteristics.

And it is another object of the present invention to provide a method of preparing such micelle composition, characterized by employing a functional monomer.

Further, it is a further object of the present invention to provide a pharmaceutical composition containing a hydrophobic drug in the hydrophobic core of the micelle composition.

DETAILED DESCRIPTION OF THE INVENTION

The amphiphilic block copolymer of the present invention comprises one or more of hydrophilic blocks(A) and hydrophobic blocks(B), which forms a micelle in an aqueous medium, the hydrophilic block(A) and the hydrophobic block (B) forming a shell and a core, respectively. A hydrophobic drug becomes water-soluble when the drug is introduced into the hydrophobic core of such micelle. The hydrophobic block (B) of the present invention carries 1.1 to 30 functional groups, preferably 2 to 30 functional groups, selected from the group consisting of carboxyl, amine, hydroxyl, amide, thiol and sulfonic acid groups which enhance the core's affinity to the drug. Preferably, the amount of the amphiphilic block copolymer having such functional groups is in the range of 0.1 to 10% by weight, based on the total weight of the micelle composition.

The hydrophilic block of the amphiphilic block copolymer has a molecular weight of preferably 100 to 30,000 Da, more preferably, 1,000 to 12,000 Da. The hydrophilic block of the copolymer may be a poly(alkylene oxide) or monoalkoxy poly(ethylene oxide) block, preferably, poly(ethylene oxide) or methoxy poly(ethylene oxide) block.

The hydrophobic block of the amphiphilic block copolymer is preferably biodegradable and biocompatible, and the molecular weight of the hydrophobic block is preferably from 200 to 30,000 Da, more preferably, from 1,000 to 15,000 Da. The hydrophobic block may be a polylactide, polycaprolactone, polyglycolide, copolymer of lactide and glycolide, polyorthoester, polyanhydride, polyphosphazine, poly amino acid, a mixture thereof, or a derivative thereof, preferably, a polylactide or a copolymer of lactide and glycolide.

The functional group may be a carboxyl, amine, hydroxyl, amide, thiol or sulfonic acid group. An optimal number of the functional group introduced to the hydrophobic block is 1.1 to 30, which enhances the micelle core's interaction with an essentially water-insoluble drug while maintaining a micellar form in an aqueous medium. Further, such affinity of the drug to the hydrophobic core brings out a desirable sustained-release characteristics of the drug.

Further, the amount of functional groups introduced controls the degradation rate of the micelle of the present invention. Preferably, the present invention employs a poly(ethylene oxide) as the hydrophilic block, and a polylactide or polycaprolactone as the hydrophilic block, which are non-toxic and have desired biodegradability and biocompatibility.

The amphiphilic block polymer of the present invention may be a diblock polymer of the hydrophilic block(A)-hydrophobic block(B) type, or a triblock polymer of the hydrophobic block(B)-hydrophilic block(A)-hydrophobic block (B) or hydrophilic block(A)-hydrophobic block(B)-hydrophilic block(A) copolymer type.

As one embodiment of the present invention, the amphiphilic block of formula (I) comprises a hydrophobic block containing a carefully controlled amount of functional groups:

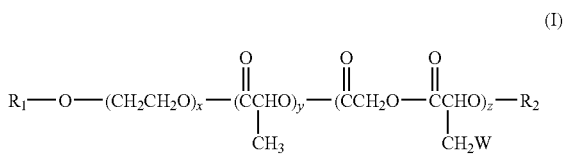

(I)

wherein $R_1$ is H, $C_{1-4}$ alkyl or $C_{1-4}$ acyl;

$R_2$ is H, $C_{1-9}$ alkyl, aryl or $C_{1-9}$ arylalkyl;

x is a number ranging from 10 to 400;

y is a number ranging from 10 to 300;

z is a number ranging from 1.1 to 30; and

W is selected from the group consisting of carboxyl, amine, hydroxyl, amide, thiol and sulfonic acid groups.

Herein, x, y or z represent the average number of repeating units of the polymer.

Preferably, the amphiphilic block of formula (I) comprises a hydrophobic block wherein W is a carboxyl group. Preferably, z is the number ranging from 2 to 30. The amphiphilic block of formula (I) comprises a hydrophobic block wherein a ratio z/y preferably ranges from 0.015 to 2, more preferably from 0.02 to 1.5.

The amphiphilic block copolymer of the present invention may be prepared by introducing a controlled amount of functional groups into the hydrophobic block(B) to enhance the core's affinity to a hydrophobic drug.

As one embodiment of the present invention, the amphiphilic block copolymer of formula (I) is prepared as follows:

In the presence of a polyethyleneoxide or monomethoxy-polyethyleneoxide, a heterocyclic ester of D,L-lactide is reacted with 3-{(bezyloxycarbonyl)methyl}-1,4-dioxane-2,5-dione (BMD, a functional monomer), to obtain an amphiphilic block copolymer, the hydrophobic block thereof comprising benzyl groups, followed by hydro-debenzylation under hydrogen in the presence of a catalyst to obtain an amphiphilic block copolymer comprising carboxyl groups (see *International Journal of Biological Macromolecules*, 1999, 25, 265).

The functional monomer, 3-{(bezyloxycarbonyl)methyl}-1,4-dioxane-2,5-dione (BMD), may be prepared by benzylation of the carboxyl group of aspartic acid in the presence of an acid catalyst and then replacing the amine group with a hydroxyl group. Then, the resultant is bromoacetylated in the presence of a base catalyst to obtain the cyclic structure of BMD (see *Macromolecules*, 1988, 21, 3338).

In accordance with one aspect of the present invention, there is provided a pharmaceutical micellar composition having a core-shell structure, the hydrophobic core of the micelle being designed to load a hydrophobic drug to a higher capacity.

The micellar composition and a drug are dissolved in an organic solvent, and then, the organic solvent is replaced with water, e.g., by dialysis, to obtain an aqueous micelle solution containing the drug. Then, the solution is lyophilized, sterilized and sealed to obtain a pharmaceutical micelle composition containing the drug.

The drug may be present in an amount ranging from 0.1 to 5% by weight based on the total weight of the pharmaceutical composition. A drug having a solubility of not more than 10 mg/ml may be employed. The drug may be an anti-cancer drug, antiflammation, sex hormone, steroid, anti-hypertensive drug or anti-emesis drug. Preferably, the drug may be paclitaxel, camptothecin, biphenyl dimethyl dicarboxylate, piposulfan, danazole, taxotere, adriamycin, indomethacin, etoposide, itraconazole, nystatin, hemoglobin or omeprazole.

One embodiment of the medicinal composition of the present invention can be prepared as follows:

10 to 500 mg of the amphiphilic block copolymer of formula I and 2 to 200 mg of a drug, e.g. paclitaxel, adriamycin or indomethacin, are dissolved in 2 to 50 ml of an organic solvent, e.g. tetrahydrofuran or dimethylformamide, and 10 to 100 ml of distilled water is added thereto. Then, the mixture is stirred for 12 to 36 hours and dialyzed to obtain an aqueous micelle solution containing the drug in the hydrophobic core of the micelle. The aqueous micelle solution may be lyophilized, sterilized and sealed to obtain a pharmaceutical composition for injection.

The micelle composition may be administrated orally or parenterally, for example by injection, for example at a drug concentration of 0.01 to 5 mg/ml.

The micelle composition of the present invention has a markedly increased drug loading capacity, and sustained-drug release characteristics.

The present invention is further described in the following Examples which are given only for the purpose of illustration, and are not intended to limit the scope of the invention.

Preparation of the Amphiphilic Block Copolymers

Preparation Example 1

A mixture of 4.0 g of methoxy poly(ethylene oxide) (M.W.=5000), 5.7 g of D,L-lactide recrystallized from ethyl acetate, 0.3 g of 3-{(bezyloxycarbonyl)methyl}-1,4-dioxane-2,5-dione (BMD, a functional monomer), and 40 mg of stannous octoate (a catalyst) was placed in a round-bottomed flask and evaluated for 30 min. to achieve a pressure of 0.001 mmHg. Then, the mixture was allowed to polymerize at 168° C. for 2 hours to obtain a diblock copolymer of poly(ethylene oxide-b-lactide), the benzyl groups being introduced into the polylactide block. 4 g of the resultant block copolymer was dissolved 125 ml of dioxane in an Erlenmeyer flask, and 1 g of a Pt/C catalyst was added thereto. The flask was filled with hydrogen, and then the mixture was allowed to undergo hydro-debenzylation at room temperature, to obtain a diblock copolymer of poly(ethylene oxide-b-lactide), having carboxyl groups introduced into the polylactide block. Nuclear magnetic resonance(NMR) spectroscopy was performed to determine the values of x, y and z from the intensity of each peak of NMR, respectively. The structure of the block copolymer is shown below:

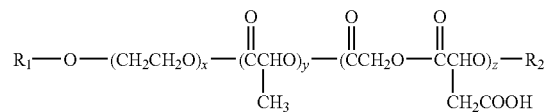

wherein $R_1$ is $CH_3$; $R_2$ is H; x=113; y=55.7; z=1.34; and z/y=0.0241.

Preparation Example 2

A poly(ethylene oxide-b-lactide) diblock copolymer was prepared by repeating the procedure of Preparation Example 1, except for employing 4.0 g of methoxy poly(ethylene oxide)(M.W.=5000), 5.4 g of D,L-lactide recrystallized from ethyl acetate, and 0.6 g of BMD. The structure of the block copolymer is the same as a preparation Example 1, except for x=113; y=49.4; z=2.78; and z/y=0.0563.

Preparation Example 3

A poly(ethylene oxide-b-lactide) diblock copolymer was prepared by repeating the procedure of Preparation Example 1, except for employing 4.0 g of methoxy poly(ethylene oxide)(M.W.=5000), 5.1 g of D,L-lactide recrystallized from ethyl acetate, and 0.9 g of BMD. The structure of the block copolymer is the same as a preparation Example 1, except for x=113; y=38.2; z=3.74; and z/y=0.0979.

Preparation Example 4

A poly(ethylene oxide-b-lactide) diblock copolymer was prepared by repeating the procedure of Preparation Example 1, except for employing 4.0 g of methoxy poly(ethylene oxide)(M.W.=5000), 4.0 g of D,L-lactide recrystallized from ethyl acetate, and 2.0 g of BMD. The structure of the block copolymer is the same as a preparation Example 1, except for x=113; y=33.3; z=11.5; and z/y=0.345.

Preparation Example 5

A poly(ethylene oxide-b-lactide) diblock copolymer was prepared by repeating the procedure of Preparation Example 1, except for employing 4.0 g of methoxy poly(ethylene oxide)(M.W.=5000), 2.0 g of D,L-lactide recrystallized from ethyl acetate, and 4.0 g of BMD as the functional monomer. The structure of the block copolymer is the same as a preparation Example 1, except for x=113; y=16.7; z=23.0; and z/y=1.38.

Comparative Preparation Example 1

A poly(ethyleneoxide-b-lactide) diblock copolymer was prepared by repeating the procedure of Preparation Example 1, except for employing 4.0 g of methoxy poly(ethylene oxide)(M.W.=5000) and 6.0 g of D,L-lactide recrystallized from ethyl acetate, without adding BMD. The structure of the block copolymer is the same as a preparation Example 1, except for x=113; y=56.1; z=0; and z/y=0

Comparative Preparation Example 2

A poly(ethylene oxide-b-lactide) diblock copolymer was prepared by repeating the procedure of Preparation Example 1, except for employing 4.0 g of methoxy poly(ethylene oxide)(M.W.=5000) and 6.0 g of BMD, without adding D,L-lactide. The structure of the block copolymer is the same as a preparation Example 1, except for x=113; y=0; and z=30.3.

Physicochemical Properties of the Diblock Copolymers

Physicochemical properties of the amphiphilic copolymers prepared in Preparation Examples 1 to 5 and Comparative Examples 1 and 2 were evaluated. Nuclear magnetic resonance spectroscopy and gel permeation chromatography were used to determine the poly(ethylene oxide) (PEO)/polylactide (PLA) weight ratio and the molecular weight, respectively (see Table 1).

TABLE 1

| | y | z | z/y | Weight ratio (wt %) (PEO/PLA) | M.W. | M.W. Distribution (PDI) |
|---|---|---|---|---|---|---|
| Preparation Example 1 | 55.7 | 1.34 | 0.0241 | 54.1/45.9 | 10000 | 1.14 |
| Preparation Example 2 | 49.4 | 2.78 | 0.0563 | 55.3/44.7 | 9010 | 1.14 |
| Preparation Example 3 | 38.2 | 3.74 | 0.0979 | 59.5/40.5 | 8480 | 1.14 |
| Preparation Example 4 | 33.3 | 11.5 | 0.345 | 53.2/46.8 | 10500 | 1.13 |
| Preparation Example 5 | 16.7 | 23.0 | 1.38 | 49.0/51.0 | 10200 | 1.13 |
| Comparative Preparation Example 1 | 56.1 | 0 | 0 | 55.3/44.7 | 10500 | 1.13 |
| Comparative Preparation Example 2 | 0 | 30.3 | — | 48.7/51.3 | 10700 | 1.14 |

Preparation of the Medicinal Agent Compositions

Examples 1 to 5

100 mg of each copolymer prepared in Preparation Examples 1 to 5, and 50 mg of paclitaxel were dissolved in 10 ml of dimethylformamide. Then, 10 ml of distilled water was added thereto and the mixture was stirred for 24 hours. The resultant mixture was put into a dialysis bag and placed in distilled water for 24 hours to obtain a pharmaceutical composition containing paclitaxel.

Comparative Examples 1 and 2

Pharmaceutical compositions containing paclitaxel were prepared by using the copolymers prepared in Comparative Preparation Examples 1 and 2, respectively, by the same method of Example 1.

Physical Properties of the Medicinal Agent Compositions

The drug release rate of each of the compositions prepared in Examples 1 to 5 and Comparative Examples 1 and 2 was measured according to the procedure described in the 2nd volume of Korea Pharmacopeia.

Each micelle containing paclitaxel was homogenously dissolved in 10 ml of a dissolution solution (phosphate buffer, pH 7.4), and then the resultant solution was dialyzed by using a dialysis membrane (molecular weight cutoff, MWCO=8, 000). Every hour, 1 ml of the drug solution released through the membrane was taken and 1 ml of the phosphate buffer was added thereto. Then, the resultant solution was diluted with 2 ml of acetonitrile, and quantified by HPLC to determine the drug release rate.

Table 2 shows the micelle diameter, the saturation drug content, the drug release time and the degradation time of the micelle containing paclitaxel. The micelle diameter and the saturation drug content were measured by dynamic light scattering and UV spectrometer, respectively. The drug release time is defined by the time required for releasing 50% of the drug.

TABLE 2

| | Micelle diameter (nm) | Saturation drug content (wt %) | Drug release time (hr) | Degradation time of the micelle (day) |
|---|---|---|---|---|
| Example 1 | 30.0 | 8.0 | 21 | 10 |
| Example 2 | 28.0 | 13.7 | 40 | 7 |
| Example 3 | 34.8 | 14.9 | 52 | 6 |
| Example 4 | 31.3 | 16.9 | 59 | 5 |
| Example 5 | 28.5 | 16.8 | 60 | 4 |
| Comparative Example 1 | 42.8 | 3.8 | 8 | 20 |
| Comparative Example 2 | — | — | — | — |

As can be seen from Tables 1 and 2, the micelles of Examples 1 to 5 have a diameter of about 30 nm, which is appropriate for an injectable drug delivery system.

Each of the compositions of Examples 1 to 5 contained a higher amount of the drug in the hydrophobic core than that of Comparative Example 1. For example, the saturation drug content of the composition of Example 3 (z=3.74, z/y=0.0979) was approximately 4-fold higher than that of Comparative Example 1 (z=0).

With more carboxyl groups introduced into the hydrophobic block, the drug release time becomes longer. Therefore, by controlling the amount of carboxyl group introduced, one can adjust the sustained-release characteristics of the composition. Further, with increasing the number of carboxyl groups introduced, the micelle degradation time becomes shorter. Accordingly, a micelle composition having more carboxyl groups will rapidly degrade after releasing the drug.

However, if the block copolymer contained too much carboxyl groups (z>30), it fails to form a micelle (see Comparative Example 2 of Table 2), and thus, such copolymer is not suitable for drug delivery system.

It can be seen from the above results, when from 1.1 to 30 carboxyl groups are introduced into the hydrophobic block of the amphiphilic copolymer, the micelle therefrom can carry a large amount of a hydrophobic drug, and exhibit sustained-release characteristics.

While the embodiments of the subject invention have been described and illustrated, it is obvious that various changes and modifications can be made therein without departing from the spirit of the present invention which should be limited only by the scope of the appended claims.

What is claimed is:

1. A micelle composition for drug deliver system comprising an amphiphilic block copolymer represented by formula (1):

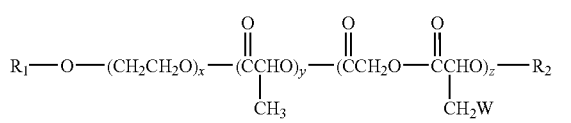

wherein $R_1$ is H, $C_{1-4}$ alkyl or $C_{1-4}$ acyl;
$R_2$ is H, $C_{1-9}$ alkyl, aryl or $C_{1-9}$ arylalkyl;
x is a number ranging from 10 to 400;
y is a number ranging from 10 to 300;
z is a number ranging from 1.1 to 30;
a ratio, z/y ranges from 0.015 to 2; and
W is selected from the group consisting of carboxyl, amine, hydroxyl, amide, thiol and sulfonic acid groups.

2. The composition of claim 1, wherein W is a carboxyl group.

3. The composition of claim 1, wherein the ratio z/y ranges from 0.02 to 1.5.

4. A pharmaceutical micelle composition comprising a hydrophobic drug introduced in the micelle composition according to any one of claims 1, 2 and 3.

5. The composition of claim 4, wherein the drug is selected from the group consisting of paclitaxel, camptothecin, biphenyl dimethyl dicarboxylate, piposulfan, danazole, taxotere, adriamycin, indomethacin, etoposide, itraconazole, nystatin, and omeprazole.

6. The composition of claim 4, wherein the drug is present in an amount ranging from 0.1 to 5% by weight, based on the total night of the micelle composition.

* * * * *